United States Patent
Collora et al.

(10) Patent No.: US 10,321,686 B2
(45) Date of Patent: Jun. 18, 2019

(54) FREEZE DRIED SCENT LURE

(71) Applicant: American Outdoors, Inc., Mount Pleasant, IA (US)

(72) Inventors: Samuel C. Collora, Mount Pleasant, IA (US); Judith C. Collora, Mount Pleasant, IA (US)

(*) Notice: Subject to any disclaimer, the term of this patent is extended or adjusted under 35 U.S.C. 154(b) by 0 days.

(21) Appl. No.: 15/663,250

(22) Filed: Jul. 28, 2017

(65) Prior Publication Data

US 2019/0029264 A1 Jan. 31, 2019

(51) Int. Cl.
*A01M 31/00* (2006.01)
*A01N 63/02* (2006.01)

(52) U.S. Cl.
CPC ........... *A01N 63/02* (2013.01); *A01M 31/008* (2013.01)

(58) Field of Classification Search
None
See application file for complete search history.

(56) References Cited

U.S. PATENT DOCUMENTS

| 5,896,692 A | 4/1999 | Collora et al. |
| 2005/0247782 A1* | 11/2005 | Ambartsoumian ..... B01L 3/545 235/385 |
| 2006/0263326 A1* | 11/2006 | Weiser ..................... A01N 1/00 424/74 |
| 2017/0318800 A1* | 11/2017 | Krohn ................. A01M 31/008 |

* cited by examiner

*Primary Examiner* — Robert A Wax
*Assistant Examiner* — Randeep Singh
(74) *Attorney, Agent, or Firm* — McKee, Voorhees & Sease, PLC

(57) ABSTRACT

A dry urine-based scent lure is provided for hunting. The lure includes an absorbent member impregnated with liquid urine, and then freeze dried to remove moisture from the host member. The urine maybe a blended mixture from different animals so as to have desired properties. The urine is concentrated and then infused into the absorbent material, which is then flash frozen, followed by freeze drying. The resulting dry scent lure is packaged so as to seal out humidity, and produce a lure with unlimited shelf life.

17 Claims, 1 Drawing Sheet

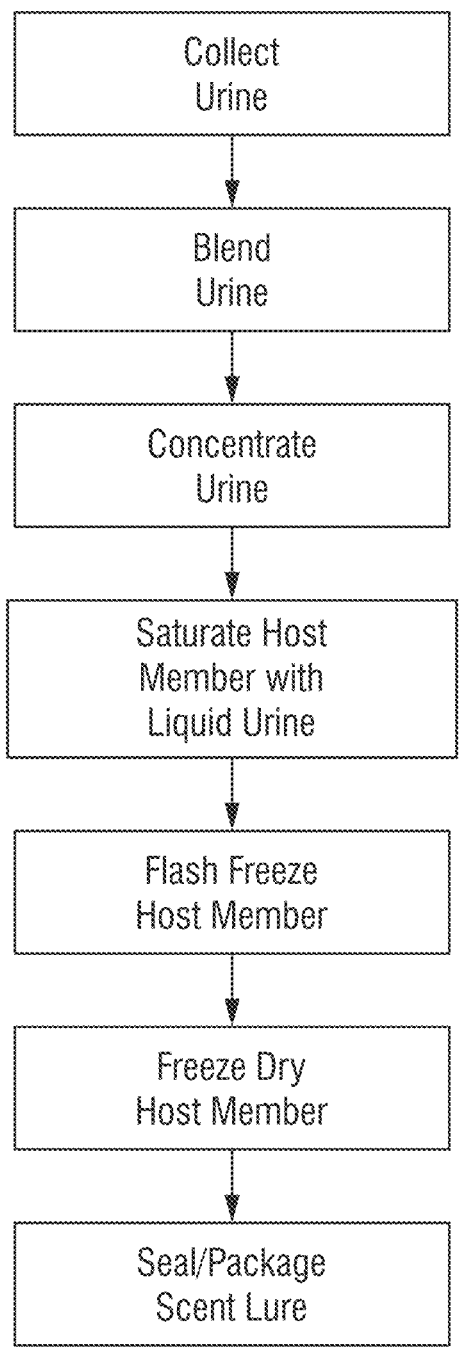

FREEZE DRIED SCENT LURE

FIELD OF THE INVENTION

The present invention is directed towards a urine-based hunting scent lure and a freeze drying process for making the lure. In particular, the lure comprises an absorbent host member infused with liquid urine and then freeze dried to drive out the moisture from the host member.

BACKGROUND OF THE INVENTION

Hunting scent lures are well-known to attract deer and other members of the cervidae family to a hunter's site. One of the most common scent lures utilizes doe urine to attract a buck to an area close to the hunter to allow the hunter to take a shot at the buck.

Urine based scent lures typically come in a liquid form or a powdered form. The urine for the liquid lures must be collected shortly before or during the hunting season, which typically is in the fall. Estrus urine and buck rut urine is often desirable, but can only be collected during the breeding cycle of the deer. Thus, production of liquid urine based lures using these special urines is limited in time. Liquid lures also must be carefully handled, during production, retail, and in the field. Liquid lures typically have a shelf life of approximately 3 months. Preservatives may be added to increase the shelf life, but may alter the smell of the product. Liquid lures may be refrigerated to slow bacteria growth and increase shelf life modestly.

Freeze drying urine into powdered form overcomes many of the problems of liquid scent lures. U.S. Pat. No. 5,896,692 describes a freeze dried scent lure product and process. The freeze drying process creates powdered urine which has indefinite shelf life, and which simplifies handling as compared to liquid lures. Preferably, the powdered freeze dried urine is rehydrated by the hunter at the time of use. Ideally, rehydration uses distilled water, spring water, snow or other unprocessed water. Thus, the hunter may need to bring bottled water on the hunt. When the powdered scent lure is rehydrated, the lack of any structural boundaries allows the hydrated powder to run off from an initial or desired location. The powdered freeze dried lure is also subject to spillage, which is undesirable.

Therefore, there is a need for an effective scent lure which overcomes the problems of liquid and powdered scent lures.

A primary objective of the present invention is the provision of an improved urine-based scent lure.

Another objective of the present invention is the provision of a hunting scent lure comprising an absorbent member impregnated with urine and then freeze dried to remove moisture from the member.

A further objective of the present invention is the provision of a method of producing a hunting scent lure using liquid urine infused into an absorbent host member.

Another objective of the present invention is the provision of a scent lure including animal urine so as to be effective in attracting the desired game animal to the hunter.

Still another objective of the present invention is a provision of a urine-based scent lure which retains the odoriferous ingredients of the animal urine.

Yet another objective of the present invention is the provision of a urine-based scent lure which retains the original structure, chromosomes, cell count and hormones of the animal urine.

A further objective of the present invention is a provision of a solid and dry hunting scent lure which is free from preservatives.

Still another objective of the present invention is a provision of a urine-based scent lure which maintains the natural pheromones of the animal urine.

Another objective of the present invention is a provision of a solid scent lure which can be placed in and maintained in any location.

A further objective of the present invention is the provision of a urine-based scent lure which is economical to manufacture, easy to handle, and has unlimited shelf life.

These and other objectives have become apparent from the following description of the invention.

SUMMARY OF THE INVENTION

The hunting scent lure comprises an absorbent host member impregnated or infused with concentrated liquid urine, or a urine blend, and then freeze dried so as to drive the moisture out of the host member. The freeze dried product can then be sealed and packaged, with an indefinite shelf life before use by a hunter.

The process for creating the solid scent lure starts with collection of animal urine, free from contaminates. The urine may be blended from multiple animals. The urine is concentrated, and then applied to an absorbent host member to a point of saturation. The host member is then placed in an ultra-low temperature freezer to freeze the saturated member into a solid. The frozen member is then placed in a freeze dryer to drive moisture out of the member. After freeze drying, the host member is packaged so as to seal out humidity and moisture.

BRIEF DESCRIPTION OF THE DRAWINGS

FIG. 1 is a flow chart showing the method for producing the hunting scent lure, according to the present invention.

DETAILED DESCRIPTION OF THE INVENTION

Urine is collected in known manners so as to be free from contaminates, such as feces. Urine from different animals maybe blended to produce a liquid mixture with the desired properties. For example, doe or cow urine may be mixed with buck or bull urine. The urine may be collected at desirable times, such as estrus urine and rut urine during the breeding cycle. Natural additives maybe added to the urine, such as glands and glandular secretions.

The collected and/or blended urine is then processed to concentrate the urine. One example of the concentration process involves inverting the urine-containing vessel over a catch vessel, and then freezing the urine for approximately 8 hours. The frozen urine can then be thawed and then weep out a portion of the thawed urine to produce a concentrated liquid urine having a dark color and a strong, pungent scent or aroma. This concentration process may take 72 hours. The residual ice is discarded. The urine concentration step reduces subsequent freeze drying time, since a portion of the moisture is removed by the concentration process.

The concentrated urine is then placed in a vessel or container having one or more absorbent host members. The host members maybe any absorbent material which will not dissolve or degrade when saturated with the urine. For example, the host member may be a wick, a pad, a sponge, a felt material, or other cloth material. When multiple host members are used, these members should be placed in the vessel or container in a manner to simplify separation after the freeze drying process. For example, if wicks are used, the wicks can be placed in perpendicular layers to one another, or maybe stood parallel to one another within the container. The container should have sufficient urine so as to soak the host members to a saturated condition. The vessel maybe rotated or shaken to assure consistent distribution of the urine through the host members, as so as to expedite saturation time.

The vessel with the saturated host members is then placed in an ultra-low temperature freezer so as to freeze the host members. Urine does not freeze easily, due to the presence of salt. Concentrated urine retains the salt, which makes freezing more difficult. Thus, conventional food product freezers are not cold enough to freeze the contents of the vessel. For example, the freezer should have a temperature that can be lowered to at least −70° F. The freezing process may take up to 36 hours, or longer. As an alternative to an ultra-low-temperature freezer, the vessel maybe imbedded in dry ice, which typically has a temperature of approximately −109° F., until the host members are frozen solid. This preliminary freezing step minimizes the time required for the next freeze drying step.

The host members are then placed into a freeze dryer, which is run for a sufficient time to drive the moisture out of the host products, and thereby produce a dry scent lure. The host members may be separated before or after the freeze drying process. Once freeze dried, the host members are sealed to keep out moisture and humidity. The sealed product has an unlimited shelf life, and does not require refrigeration to preserve freshness.

In use, a hunter can take the sealed package to the hunting site. The package is then unsealed and the dry host member can be placed in any convenient location. The host member does not require rehydration, due to the strong concentrated aroma. The host member will remain in position wherever placed by the hunter. For example, the solid scent lure of the present invention can be placed on the ground, hung on a branch, dragged along the ground to create a scent line, or placed in or on a decoy. Each impregnated host member is a complete unit and will stay wherever positioned. If desired, the hunter can rehydrate the host member, which will absorb the water without run off.

The freeze drying process retains all of the odiferous ingredients and pheromones from the liquid urine, so as to be highly attractive to a buck. The freeze drying process eliminates the need for preservatives, as in liquid scent lures, and eliminates the need for refrigeration.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A hunting scent lure, comprising:
   a host member impregnated with concentrated liquid urine and then frozen, followed by freeze drying to drive moisture out of the member while retaining a sufficiently strong aroma to attract an animal; and
   the host member being a unitary piece after freeze drying for use without rehydration.

2. The hunting scent lure of claim 1 wherein the host member is an absorbent material.

3. The hunting scent lure of claim 1 wherein the liquid urine can be a blend from different animals.

4. The hunting scent lure of claim 1 wherein the host member retains all the odiferous ingredients of the liquid urine.

5. The hunting scent lure of claim 1 wherein the liquid urine is free of preservatives.

6. The hunting scent lure of claim 1 wherein the liquid urine is substantially free from contaminants.

7. The hunting scent lure of claim 1 wherein the liquid urine is substantially free from feces.

8. A method of producing a dry scent lure comprising:
   infusing concentrated liquid urine into a host member; then
   freezing the host member to a solid state; and then
   placing the frozen host member into a freeze dryer to drive out moisture while maintaining a urine scent in the host member for use without rehydrating.

9. The method of claim 8 wherein the freezing step is at a maximum temperature of −70° F.

10. The method of claim 8 wherein the member is frozen using dry ice.

11. The method of claim 8 wherein the member is frozen using an ultra low temperature freezer.

12. The method of claim 8 wherein the host member is saturated with the liquid urine.

13. The method of claim 8 wherein the host member is soaked in the liquid urine.

14. The method of claim 8 further comprising, as a first step, blending urine from different animals.

15. The method of claim 8 further comprising sealing the host member in a vessel containing the liquid urine.

16. The method of claim 15 further comprising rotating the vessel to saturate the host member with the urine.

17. The method of claim 8 further comprising sealing the host member after freeze drying to preclude humidity absorption prior to use of the scent lure.

* * * * *